United States Patent [19]

Vacek et al.

[11] 4,101,558

[45] Jul. 18, 1978

[54] PROCESS FOR PREPARING THIOXANTHONES

[75] Inventors: Lubomir Vacek, Toledo; Harold M. Foster, Sylvania, both of Ohio

[73] Assignee: The Sherwin-Williams Company, Cleveland, Ohio

[21] Appl. No.: 789,465

[22] Filed: Apr. 21, 1977

[51] Int. Cl.$^2$ .......................................... C07D 335/16
[52] U.S. Cl. .................................................. 260/328
[58] Field of Search ......................... 260/328, 590 FB

[56] References Cited

U.S. PATENT DOCUMENTS

| | | | |
|---|---|---|---|
| 2,692,898 | 10/1954 | Beyerman et al. | 260/591 |
| 3,836,585 | 9/1974 | Tristram et al. | 260/590 |
| 3,950,342 | 4/1976 | Gorvin | 260/279 R |

OTHER PUBLICATIONS

Davis, et al., C. A. 4:3073-3074, (1910).
Buess, et al., Synth. Meth. of Org. Chem., vol. 7, (1953), #644.
Kharasch, et al., Synth. Meth. of Org. Chem., vol. 10, (1956), #475.

*Primary Examiner*—Cecilia M. Jaisle
*Attorney, Agent, or Firm*—James V. Tura; Neil A. DuChez

[57] ABSTRACT

This invention is directed to a process of preparing thioxanthones derived from ortho-chlorosulfenylbenzoyl chloride and aromatic compounds in the presence of Friedel-Crafts catalyst.

20 Claims, No Drawings

PROCESS FOR PREPARING THIOXANTHONES

This invention relates to a process for preparing thioxanthones and more particularly substituted thioxanthones such as the chloro-substituted thioxanthones. The thioxanthones of this invention are prepared by the condensation reaction of orthochlorosulfenylbenzoyl chloride and at least one aromatic compound in the presence of a Friedel-Crafts catalyst in an organic medium. The thioxanthen-9-ones are particularly useful as intermediates in the preparation of various drugs including, for example, the psychotheraputics, antinauseants, central depressants, antiparasitic drugs, drugs for the treatment of allergic conditions, antihistamines and the like.

In addition, various derivatives of thioxanthen-9-one are being used as activators or sensitizers in the photopolymerization of ethylenically unsaturated monomers. These photopolymerizable compositions, which cure on exposure to radiation, are useful as vehicles in surface coatings such as paint, enamel, lacquer, varnish and the like. The alkyl, alkoxy and hydroxy substituted thioxanthones are particularly useful as heat and ultraviolet stabilizers for the polyolefins.

Presently, thioxanthen-9-one and its derivatives are prepared by cyclization of the corresponding ortho-(phenylthio)-benzoic acid and its derivative in the presence of concentrated sulfuric acid. However, certain nitro derivatives of this acid, for example, will not cyclize in the present of concentrated sulfuric acid and, therefore, the ring closure is accomplished through conversion to the corresponding acid chloride, by means of $PCl_5$, $SOCl_2$, etc. followed by reaction with aluminum chloride. More recently, thioxanthen-9-ones are obtained by the use of nitriles in place of the carboxylic acid wherein the cyclization is carried out in the presence of polyphosphoric acid, see Journal of Organic Chemistry, Vol. 38, pgs. 1743–1746 and German Pat. No. 2,344,799. A method which does not follow the above-mentioned reaction mechanism utilizes oxalyl chloride as a source of the carbonyl and a corresponding diarylthioether as the basic molecular component. Both of these methods, however, are of limited importance and at the present time the use of ortho-(phenylthio)benzoic acid and its derivatives are the primary intermediate used for the commercial production of thioxanthen-9-one. The intermediate, i.e. ortho-phenylthiobenzoic acid is obtained by using the Ullman condensation, i.e. the condensation of thiosalicylic acid with an aromatic halo-compound or alternatively by the reaction of ortho-halobenzoic acid with thiophenols in a basic medium and in the presence of copper catalysts. These preparation procedures have been intensely studied in the past but no new concepts or basic improvements have been developed.

Thus, with the exception of the method wherein ortho-iodobenzoic acid is condensed with para-chlorothiophenol and 2-(4'-chlorophenylthio)benzoic acid is isolated in yields of about 97% based on starting iodobenzoic acid, the average yield of these compounds range only from about 45 to 65%. Consequently, because all these methods for preparing thioxanthones involve various technical obstacles, particularly where the reactions are carried out on a large scale, the isolated products require further purification, and not readily available chemicals have to be used, the procedures heretofore offer no commercial advantages.

Another process for the preparation of thioxanthen-9-one is based on the condensation of thiosalicylic, ortho-sulfinobenzoic and 2,2'-dithiodibenzoic acid and derivatives thereof with unsubstituted or correspondingly substituted aromatic compounds in a medium containing sulfuric acid; see Journal of American Chemical Society, Vol. 74, (1952), pgs. 4296–4309; J.C.S., Vol. 97, pgs. 1297 and J.C.S., Vol. 97, pages 1290–1299.

This method involves substantially the same chemical principles as mentioned hereinabove wherein in the first stage of the process the intermediate, i.e. 2-(phenylthio)-benzoic acid or its derivatives are formed through arylthiolation of the aromatic ring followed with cyclization with sulfuric acid. Where 2,2'-dithiodibenzoic acid is used as the starting material, thioxanthones are obtained in yields ranging from 45–60% of theory. Moreover, in addition to low production yields the method has many other inherent disadvantages. For example, a large amount of the concentrated sulfuric acid required for the reaction has to be diluted with water during quenching of the product. The disposal of such large amounts of sulfuric acid creates problems and to recover and reuse the acid is difficult and expensive. Another technological obstacle is the filtration of the quenched product from the highly acidic medium in that the filtration is extremely slow. Moreover, the reaction requires comparatively long reaction times, e.g. from 8–12 hours, if maximum yields are to be obtained and the aromatic compound which is to be arylthiolated, must be used in considerable excess because sulfonation of this compound is difficult to suppress. Moreover, because sulfuric acid also acts as an oxidizing agent, sulfur dioxide evolves from the reaction mixture during the process and, therefore, requires a scrubbing step.

Thus, to avoid these technical problems and to provide a process for preparing thioxanthones in higher yields at less cost, it has been found that the thioxanthone and the substituted thioxanthones can be prepared by condensing an ortho-chlorosulfenylbenzoyl chloride or a derivative thereof with at least one aromatic compound, in the presence of a Friedel-Crafts catalyst in an organic medium. More specifically, the reaction mechanism is illustrated hereinbelow.

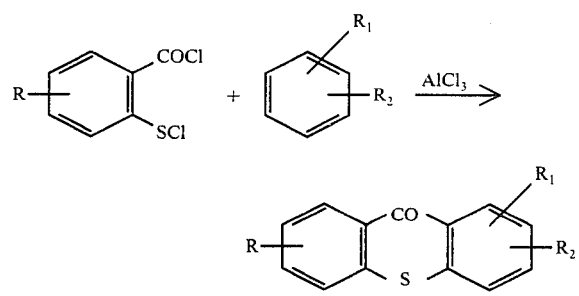

wherein R, is selected from the class consisting of hydrogen, chlorine, bromine, aryl, lower alkyl and lower alkoxy radicals having 1 to 8 carbon atoms and $R_1$ and $R_2$ are either the same or different from one another and are selected from the class consisting of hydrogen, chlorine, bromine, hydroxyl, aryl, lower alkyl and lower alkoxy radicals having 1 to 8 carbon atoms. Specific examples of thioxanthones include 2-chlorothioxanthone, 2-bromothioxanthone, 2,7-dichlorothioxanthone, 2-hydroxythioxanthone 2-methylthioxanthone, 2-chloro-6-methylthioxanthone, etc.

The aromatic compound may include the polynuclear aromatic compounds such as biphenyl, naphthalene, etc. The process is carried out in an organic medium comprising various organic solvents which are particularly known to be useful for Friedel-Crafts reactions such as methylene chloride, ethylene chloride, 1,1,2,2-tetrachloroethane, etc. Moreover, the medium may include the reactant (aromatic compound) such as benzene, chlorobenzene, ortho-dichlorobenzene, bromo benzene, ortho-dibromobenzene, the alkylated benzenes such as toluene, isopropylbenzene, etc. alkyl phenols such as 4-methylphenol, 2-tert-butyl-4-methylphenol, etc. phenyl ethers such as anisole, etc.

The ortho-chlorosulfenylbenzoyl chloride may be conveniently obtained by well known methods, including, for example, the reaction of 2,2'-dithiodibenzoic acid or its ring substituted derivatives through the conversion to the acid chloride by the use of $SOCl_2$ or a similar reagent followed by cleavage of the S-S group by chlorination. It was found that approximately one chemical equivalent of the Friedel-Crafts catalyst, i.e. aluminum chloride for each mole of the ortho-chlorosulfenylbenzoyl chloride was sufficient to obtain satisfactory yields. The use of more catalyst, e.g. aluminum chloride had not advantage or influence in the yield of the thioxanthone, but the use of lesser amounts may result in lower yields.

The reaction temperatures during the addition of the reactants, are maintained in the range of about 10° to 40° C and more preferably 15° to 25° C. The catalyst, i.e. aluminum chloride is gradually charged to the reaction mixture over a period of 30-40 minutes and following the addition, the temperature may be elevated to the range of 40° to 80° C. The increased reaction temperature, following the charge of the reactants, accelerates the reaction and helps free the system of hydrogen chloride gas generated during the reaction.

The method of isolating the product from the reaction mixture may vary depending on the physical and chemical character of the thioxanthone and on the degree of purity required of the product. Some of the complexes formed between the aluminum chloride and the product are soluble in the reaction mixture while others are less soluble or insoluble. Separation of the insoluble complexes may be part of the purification process. The decomposition of such separated complexes usually provides very pure compounds. The soluble complexes may be decomposed while still in solution in the reaction medium or after removal of the solvent. Decomposition of the complex can be accomplished with water, with diluted mineral acid or with aqueous solutions of alkaline hydroxides, e.g. sodium, potassium, barium or calcium hydroxide. The use of one or the other of these reagents to decompose the complex mostly depends upon the physical and chemical character of the produced thioxanthone. For example, for the alkali insoluble products, the use of alkali hydroxide solutions were found to be superior to the use of some of the other means of decomposing the complex. In the case of hydroxylated products, however, water or acid decomposition may be preferred.

The following examples illustrate the process for preparing thioxanthones in accordance with this invention.

EXAMPLE 1

Preparation of 2- and 4- Chlorothioxanthen-9-One

A 2000 ml three-neck flask equipped with an agitator, a thermometer, a gas introduction tube, a dropping funnel, a reflux condenser sealed on the open end with gas bubbler was charged with 153.2 g (0.5 mole) of 2,2'-dithiodibenzoic acid, 1000 ml of chlorobenzene and approximately 0.5 ml of dimethylformamide. The agitated slurry was heated to 112°–114° C and thionyl chloride in a total amount of 149 g (1.25 moles) was dropped in over a period of approximately 0.5 hr. The formed solution was cooled to 5°–10° C and 71 g of $Cl_2$ (1.0 mole) was introduced into the agitated reaction mixture over a period of 0.5 hr. The solution was then heated to 60° C and the excess of $Cl_2$ was purged with a stream of nitrogen for 10 minutes. The solution of o-chlorosulfenylbenzoyl chloride (cooled to 20° C) was ready for the next reaction step.

Into the agitated solution of o-chlorosulfenylbenzoyl chloride was gradually charged 134 g (approximately 1.0 mole) of powdered aluminum chloride over approximately 0.5 hr. at a temperature maintained in the range of 18°–22° C. When the evolution of hydrogen chloride gas slowed down (30-45 minutes after aluminum chloride charge completion) the reaction mixture was heated slowly up to 60° C. The evolution of hydrogen chloride first increased and in approximately 30 minutes ceased. After cooling to 20° C, the crystalline solids were collected by filtration, washed first with chlorobenzene and then with hexane to remove chlorobenzene. The cake was now charged into 1200 ml of 5N caustic solution, the agitated slurry was then heated to approximately 75°–80° C and held at this temperature for approximately one hour. After cooling to 20° C the pale yellow solids were filtered, washed first with weak caustic solution, then with water and dried at 110° C. Product obtained was 101.0 to 105.6 g, which was essentially pure 2-chlorothioxanthene-9-one having a m.p. of 151°–152° C. The combined chlorobenzene mother liquors were evaporated to dryness and the distillation heel was then decomposed with 200 ml of 5N caustic solution following the same procedure as described above. The isolated pale yellow product 4-chlorothioxanthen-9-one, contaminated with a small amount of 2-chloro derivative. The m.p. was 173°–175° C.

If separation of both isomers is not required, the reaction mixture after the Friedel-Crafts condensation containing $AlCl_3$ complexes can be decomposed with water. The excess chlorobenzene is then removed by steam distillation and the mixture of isomeric thioxanthones is collected by filtration. This mixture is usually contaminated with substantial amount (20-25 weight percent) of aluminum compounds and consequently requires purification such as with caustic soda digestion or crystallization from organic solvents. The mixture of isomers melts at 142°–146° C.

EXAMPLE 2

Preparation of o-Chlorosulfenylbenzoyl Chloride

A 50 ml of three-neck flask, equipped with an agitator, a thermometer, a gas introduction tube, a dropping funnel, a reflux condenser sealed on the open end with gas bubbler, was charged with 30.6 g (0.1 mole) of 2,2'-dithiodibenzoic acid, 250 ml of ethylene chloride and 6 to 8 drops of dimethylformamide. The stirred slurry was heated to reflux and 30 g (0.25 mole) of thionyl chloride was then gradually charged in approximately 1.5 hours. An additional hour heating to reflux is usually required to complete the reaction. The reaction mixture was then cooled to 8°–10° C and 15.6 g (i.e. 0.22 mile) of chlorine gas was introduced into the agitated slurry through a rotameter. The chlorination took 30–45 minutes. The temperature of 8°–10° C was maintained for additional 20 minutes, then raised to 60° C, held for 30 minutes and finally cooled to approximately 10° C.

EXAMPLE 3

Preparation of Thioxanthen-9-One

Benzene, 17.5 g (0.22 mole) was changed into the flask containing o-chlorosulfenylbenzoyl chloride in medium of ethylene chloride (Example 2). Into this well agitated mixture dry powdered aluminum chloride, (27 g or 0.2 mole), was charged in small portions at a temperature maintained in range of 10°–25° C in approximately 30 minutes. When the evolution of hydrogen chloride gas ceased, the crystalline aluminum chloride complex was filtered, the cake was washed with hexane and then portionwise was changed into 250 ml of 5N sodium hydroxide solution under cooling to maintain the temperature in range of 20°–25° C. The obtained slurry was agitated for additional 30 minutes, then filtered, the cake washed well with water and dried at 110° C. About 39 g of product was obtained which was essentially pure thioxanthen-9-one. The yield is 91% of the theory and the m.p. is 204° C.

EXAMPLE 4

Preparation of 5-Chloro-2-Chlorosulfenylbenzoyl Chloride

A 500 ml three-neck flask equipped with an agitator, a thermometer, a gas introduction tube, a dropping funnel, a reflux condenser sealed on the open end with gas bubbler was charged with 18.70 g of 5,5'-dichloro-2,2'-dithiodibenzoic acid (0.05 mole), 250 ml of ethylene chloride and 8 drops of dimethyl formamide. The agitated content of the flask was heated to reflux and at these conditions 15 g of thionyl chloride was charged dropwise over approximately 1 hour. The reaction mixture was maintained at reflux (80°–81° C) until the original slurry changed into a solution. This took 2 hours 15 minutes. The solution was then cooled to 8°–15° C (solid phase separated) and 7.8 g (0.11 mole) of chlorine gas was introduced at a rate of 0.25 g/min. The batch was agitated for an additional 30 minutes while the temperature was allowed to rise to 20°–22° C then heated to 60° C and held for 10 minutes at this temperature while slight streams of nitrogen was introduced to help strip off the excess chlorine. Cooled solution (270 ml) of 5-chloro-2-chlorosulfenylbenzoyl chloride was then ready for the next step.

EXAMPLE 5

Preparation of 2,7-Dichlorothioxanthene-9-One

One half of the solution of 5-chloro-2-chlorosulfenylbenzoyl chloride (135 ml of 0.05 mole of Example 4) was charged into 200 ml three neck flask equipped similarly as the reaction flask in Example 4. About 11.2 g of chlorobenzene was added and at the temperature of this mixture maintained in the range of 20°–30° C while 6.75 g of powdered aluminum chloride (0.05 mole) was charged in small portions in approximately 30 minutes. After the charging the batch was stirred for an additional 1 hour, while the temperature was maintained in the range of 25°–30° C. The crystalline aluminum chloride complex, which separated from the solution, was filtered and the cake was washed with hexane. The cake was then treated with 1.3 mole NaOH dissolved in 300 ml of water. The isolated product, 10 g of light yellow crystalline powder (m.p. 230C) was crude 2,7-dichloro-thioxanthen-9-one (70% yield).

High pressure liquid chromatograph (HPLC) revealed that the product contained approximately 96.5% of the title compound, approximately 2.2% of 4,7-dichloro-thioxanthen-9-one and approximately 1.3% of other impurities.

The alkaline treatment or decomposition of compounds present in the mother liquor gave 3 g of product (approximately 20% yield) containing only 49% of title compound and 46% of 4,7-dichloro isomer.

EXAMPLE 6

Preparation of 7-Chloro-2-Phenyl-Thioxanthen-9-One

A second half of the solution of 5-chloro-2-chlorosulfenylbenzoyl chloride (135 mol equivalent of 0.05 mole) prepared and described in Example 4 was placed in the same equipment as specified in Example 5, then 18.5 g of biphenyl (0.12 mole) was added and then 6.75 g of powdered aluminum chloride (0.05 mole) was charged in small portions into the solution of both reactants at a temperature maintained in range of 20°–25° C in approximately 30 minutes. The evolution of HCl, which was fast during the charging of aluminum chloride, still continued during the first part of the following one hour stirring period at 25°–30° C. Because the reaction mixture did not show the presence of filterable crystalline solids, the reaction solvent, i.e. ethylene chloride was removed by distillation and the residuum was decomposed with a solution of caustic (24 g 50% NaOH diluted with 200 ml water). After charging 300 ml of methylene chloride most of the solid phase entered in the solution, but the separation of aqueous and methylene chloride layers could be completed only after filtration of the solid phase causing the formation of a persistent emulsion. (Solid phase — product A). The separated organic layer was washed with water, dried with anhydrous magnesium sulfate and then the methylene chloride was evaprorated. The residuum containing considerable amount of unreacted biphenyl was extracted with hexane. A biphenyl-free product (Product B) was obtained as indicated below.

Isolated 10 g, i.e. 62% of the Theory

HPLC showed that Product B consisted of 93% of the title compound, 1.7% of 7-chloro-4-phenylthioxanthen-9-one and approximately 5% of impurities of unidentified composition. Product A (solids from the emulsion) 2.6 g, i.e. 12% of theory was composed of 60% of the title compound, 7.7% of 7-chloro-4-phenylthioxanthen-9-one and the remainder being compounds of unidentified composition.

While this invention has been described by a number of specific embodiments, it is obvious there are variations and modifications which can be made without departing from the spirit and scope of the invention as set forth in the appended claims.

What is claimed is:

1. A process of preparing thioxanthones which comprises reacting in the presence of effective amounts of a Friedel-Crafts catalyst approximately equal molar amounts of an ortho-chlorosulfenylbenzoyl chloride and at least one aromatic compound having the formula:

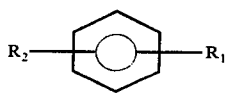

wherein $R_1$ and $R_2$ are either the same or different and selected from the class consisting of hydrogen, chlorine, bromine, hydroxyl, aryl, lower alkyl and lower alkoxy radicals having 1 to 8 carbon atoms.

2. The process of claim 1 further characterized in that the Friedel-Crafts catalyst is present in the amount of approximately 1.0 mole for each mole of the ortho-chlorosulfenylbenzoyl chloride.

3. The process of claim 1 further characterized in that ortho-chlorosulfenylbenzoyl chloride is a ring halogenated-ortho-chlorosulfenylbenzoyl chloride.

4. The process of claim 3 further characterized in that the ring halogenated ortho-chlorosulfenylbenzoyl chloride is 5-chloro-2-chlorosulfenylbenzoyl chloride.

5. The process of claim 1 further characterized in that the aromatic compound is an alkylated phenol.

6. The process of claim 5 further characterized in that the alkylated phenol is para-cresol.

7. The process of claim 1 further characterized in that the aromatic compound is an alkoxy benzene.

8. The process of claim 7 further characterized in that the alkoxy benzene is methoxy benzene.

9. The process of claim 1 further characterized in that $R_1$ is hydrogen and $R_2$ is an alkoxy radical having 1 to 4 carbon atoms.

10. The process of claim 1 further characterized in that $R_1$ is hydrogen and $R_2$ is chlorine.

11. The process of claim 1 further characterized in that the aromatic compound is naphthalene.

12. The process of claim 1 further characterized in that the aromatic compound is biphenyl.

13. The process of claim 1 further characterized in that the aromatic compound is benzene.

14. The process of claim 1 further characterized in that the aromatic compound is toluene.

15. The process of claim 1 further characterized in that the aromatic compound is a 2-tertiary-butyl-4-methylphenol.

16. The process of claim 1 further characterized in that the reaction takes place in the presence of at least one organic solvent at temperatures ranging from about 10° to 40° C.

17. The process of claim 16 further characterized in that at least one of the organic solvents is an aromatic compound.

18. The process of claim 17 further characterized in that at least one of the aromatic compounds is benzene.

19. The process of claim 18 further characterized in that at least one of the aromatic compounds is chlorobenzene.

20. The process of claim 1 further characterized in that the Friedel-Crafts catalyst is $ALCL_3$.

* * * * *